(12) United States Patent
Wi

(10) Patent No.: US 12,114,969 B2
(45) Date of Patent: Oct. 15, 2024

(54) HYPOVENTILATION MONITORING SYSTEM AND METHOD

(71) Applicant: BILAB CO., LTD., Seongnam-si (KR)

(72) Inventor: Hun Wi, Suwon-si (KR)

(73) Assignee: BILAB CO., LTD. (KR)

( * ) Notice: Subject to any disclaimer, the term of this patent is extended or adjusted under 35 U.S.C. 154(b) by 787 days.

(21) Appl. No.: 17/254,262

(22) PCT Filed: May 9, 2019

(86) PCT No.: PCT/KR2019/005545
§ 371 (c)(1),
(2) Date: Dec. 18, 2020

(87) PCT Pub. No.: WO2019/245163
PCT Pub. Date: Dec. 26, 2019

(65) Prior Publication Data
US 2021/0267480 A1    Sep. 2, 2021

(30) Foreign Application Priority Data

Jun. 18, 2018  (KR) .......................... 10-2018-0069404

(51) Int. Cl.
*A61B 5/08*    (2006.01)
*A61B 5/00*    (2006.01)
(Continued)

(52) U.S. Cl.
CPC .............. *A61B 5/0816* (2013.01); *A61B 5/01* (2013.01); *A61B 5/021* (2013.01); *A61B 5/024* (2013.01);
(Continued)

(58) Field of Classification Search
CPC ......... A61B 5/0816; A61B 5/01; A61B 5/021; A61B 5/024; A61B 5/0536;
(Continued)

(56) References Cited

U.S. PATENT DOCUMENTS

| | | | |
|---|---|---|---|
| 2010/0228143 A1* | 9/2010 | Teschner | A61B 5/0536 600/547 |
| 2016/0184518 A1 | 6/2016 | Freeman et al. | |
| 2016/0367186 A1* | 12/2016 | Freeman | A61B 5/7282 |
| 2017/0325695 A1 | 11/2017 | Freeman et al. | |

FOREIGN PATENT DOCUMENTS

| | | |
|---|---|---|
| JP | 2000312669 A | 11/2000 |
| JP | 2006034598 A | 2/2006 |

(Continued)

OTHER PUBLICATIONS

International Search Report for PCT/KR2019/005545 mailed Aug. 12, 2019.
Written Opinion for PCT/KR2019/005545 mailed Aug. 12, 2019.

*Primary Examiner* — Alyssa M Alter
(74) *Attorney, Agent, or Firm* — Renaissance IP Law Group LLP

(57) ABSTRACT

The present inventive concept relates to an apparatus and a method for providing a treatment plan by measuring the severity of sleep apnea and causes thereof. According to an embodiment of the present inventive concept, a hypoventilation monitoring system may include a an EIT data processing unit configured to generate image data on the chest of a subject by measuring either current or voltage through a plurality of electrodes attached to the subject, a ventilation parameter calculation unit configured to calculate a ventilation parameter of the subject by analyzing an image change of the chest based on the generated image data, a hypoventilation determination unit configured to determine a hypoventilation condition by comparing the calculated ventilation parameter with a hypoventilation reference value, and a display control unit configured to control a display to display at least one of the generated image data, the calculated ventilation parameter, or the determined alarm information on the hypoventilation condition.

12 Claims, 10 Drawing Sheets

(51) Int. Cl.
*A61B 5/01* (2006.01)
*A61B 5/021* (2006.01)
*A61B 5/024* (2006.01)
*A61B 5/0536* (2021.01)
*A61B 5/145* (2006.01)

(52) U.S. Cl.
CPC ........ *A61B 5/0536* (2013.01); *A61B 5/14542* (2013.01); *A61B 5/4839* (2013.01); *A61B 5/6823* (2013.01); *A61B 5/6831* (2013.01); *A61B 5/7235* (2013.01); *A61B 5/742* (2013.01); *A61B 5/746* (2013.01)

(58) Field of Classification Search
CPC .............. A61B 5/14542; A61B 5/4839; A61B 5/6823; A61B 5/6831; A61B 5/7235; A61B 5/742; A61B 5/746; A61B 5/0022; A61B 5/14551; A61B 5/318; A61B 5/7275; A61B 5/08
See application file for complete search history.

(56) References Cited

FOREIGN PATENT DOCUMENTS

| | | | |
|---|---|---|---|
| JP | 2011504119 | A | 2/2011 |
| JP | 2018011948 | A | 1/2018 |
| KR | 101650891 | B1 | 8/2016 |
| KR | 101695223 | B1 | 1/2017 |
| KR | 101765423 | B1 | 8/2017 |
| KR | 20170108462 | A | 9/2017 |
| KR | 20180056196 | A * | 5/2018 |

* cited by examiner

HYPOVENTILATION MONITORING SYSTEM AND METHOD

TECHNICAL FIELD

The present inventive concept relates to a technical idea of monitoring hypoventilation using an electrical impedance tomography (EIT) technology, and more particularly, to hypoventilation monitoring system and method capable of accurately monitoring hypoventilation-related matters such as tidal volume and a minute ventilation using an EIT image.

BACKGROUND ART

In general, in patients after surgery, respiratory depression may occur due to the influence of residual anesthetics, and in severe cases, respiratory arrest may occur, resulting in an emergency situation where it is difficult to sustain life.

Pain relievers, such as opioid and the like, which are widely used for pain relief, cause respiratory depression and in severe cases, lead to respiratory arrest to cause an emergency situation where it is difficult to sustain life.

In the treatment of various procedures such as sleep endoscopy, plastic surgery, and dental procedures, anesthetics such as propofol can cause respiratory depression and in severe cases, lead to respiratory arrest, resulting in an emergency situation where it is difficult to sustain life.

In patients with obesity hypoventilation syndrome (OHS), hypoventilation may gradually or radically worsen, resulting in an emergency situation where it is difficult to sustain life.

This is a separate symptom from obstructive sleep apnea (OSA) or central sleep apnea (CSA), and is also accompanied by OSA or CSA.

In patients with neuromuscular disease, respiratory depression may occur, and in severe cases, respiratory arrest may occur, resulting in an emergency situation where it is difficult to sustain life.

In patients with chronic obstructive pulmonary disease (COPD), respiratory depression may occur, and in severe cases, respiratory arrest may occur, resulting in an emergency situation where it is difficult to sustain life.

Therefore, it is necessary to continuously monitor hypoventilation in these patients.

Currently used methods include a spirometer, an end-tidal $CO_2$ (ETCO2) capnography, a blood oxygen saturation (SpO2) meter, and an impedance pneumography.

However, the spirometer, which requires wearing a mask or a cannula on the mouth or nose, cannot be used for continuous monitoring of hypoventilation because continuous measurement is very difficult.

On the other hand, in order to measure ETCO2, since the mask or cannula needs to be worn on the mouth or nose, continuous measurement is inconvenient and it is difficult to quickly detect hypoventilation.

In addition, in the SpO2 measurement method, in which sensors are attached to fingers, toes, and ears, continuous measurement is possible, but it is difficult to quickly detect hypoventilation.

In addition, the impedance pneumography, in which electrodes are attached to the chest to measure a change in electrical impedance of the chest according to breathing as a signal, is mainly used to measure the respiratory rate, but it is impossible to detect hypoventilation using only the respiratory rate without measuring a respiratory air volume.

Finally, although a method of measuring tidal volume and minute ventilation using the impedance pneumography is also used, but the method is vulnerable to motion artifacts and accurate measurement is difficult.

Therefore, there is a need to propose a method and a system for continuously and accurately monitoring hypoventilation.

Technical Problem

An object of the present inventive concept is to continuously monitor hypoventilation by processing and interpreting simultaneously EIT images of a cross section of the chest including the lungs, and biosignals, such as oxygen saturation, end tidal CO2, pulse wave, electrocardiogram, blood pressure, and body temperature.

An object of the present inventive concept is to improve the accuracy of measurement of tidal volume and minute ventilation by using an EIT image that provides information on air distribution and volume change in the lungs.

An object of the present inventive concept is to display the homogeneity of an air distribution in the lungs together with the tidal volume, minute ventilation, and respiratory rate based on an EIT image.

An object of the present inventive concept is to measure biosignals such as oxygen saturation, end tidal CO2, pulse wave, electrocardiogram, blood pressure, and body temperature together in addition to an EIT system for imaging and quantifying hypoventilation.

An object of the present inventive concept is to attach a plurality of electrodes at once or attach the plurality of electrodes separately by providing a sticky patch on one side of a plate.

An object of the present inventive concept is to extract information about asymmetric ventilation of both lungs and heterogeneous ventilation inside each lung from an EIT image and index and display the extracted information.

Technical Solution

According to an embodiment of the present inventive concept, a hypoventilation monitoring system may include an EIT data processing unit configured to generate image data on the chest of a subject by measuring either current or voltage through a plurality of electrodes attached to the subject, a ventilation parameter calculation unit configured to calculate a ventilation parameter of the subject by analyzing an image change of the chest based on the generated image data, a hypoventilation determination unit configured to determine a hypoventilation condition by comparing the calculated ventilation parameter with a hypoventilation reference value, and a display control unit configured to control a display to display at least one of the generated image data, the calculated ventilation parameter, or the determined alarm information on the hypoventilation condition.

According to an embodiment of the present inventive concept, the plurality of electrodes may be located at regular intervals in an elastic belt, and transmit EIT data on the measured current or voltage to the EIT data processing unit through a cable of a sensor box connected to the elastic belt.

According to an embodiment of the present inventive concept, the elastic belt may have an annular shape covering the chest of the subject, different ends of the elastic belt may be attached to and detached from the sensor box, and when attached, the plurality of electrodes may be electrically connected to the sensor box by maintaining the annular shape.

According to an embodiment of the present inventive concept, the plurality of electrodes may be included in a plurality of stickers in a preset number, and transmit the EIT data to the sensor box through an independent connection line for each of the plurality of stickers, or each of the electrodes may be attached to the subject to transmit the EIT data to the sensor box through an independent connection line for each of the plurality of electrodes.

According to an embodiment of the present inventive concept, the EIT data processing unit may detect an air distribution condition in the lungs including the symmetry of a ventilation degree of both lungs and the homogeneity of a ventilation condition of each lung from the image data.

According to an embodiment of the present inventive concept, the ventilation parameter calculation unit may calculate the ventilation parameter including tidal volume, minute ventilation, or respiratory rate by analyzing the image change.

According to an embodiment of the present inventive concept, the display control unit may control the display to display oxygen saturation, end tidal CO2, tidal volume, minute ventilation, or respiratory rate as numbers and signal graphs.

According to an embodiment of the present inventive concept, the display control unit may control the display to display the biosignal parameter including at least one of oxygen saturation, end tidal CO2, pulse wave, electrocardiogram, body temperature, and blood pressure as numbers and signal graphs.

According to an embodiment of the present inventive concept, the hypoventilation monitoring system may further include a communication unit configured to transmit the calculated ventilation parameter to at least one of a ventilator, an anesthetic machine, or a drug injector to change the operation of at least one of the ventilator, the anesthetic machine, or the drug injector.

According to an embodiment of the present inventive concept, the hypoventilation monitoring system may further include a biosignal parameter calculation unit configured to calculate a biosignal parameter by measuring a biosignal through a sensor attached to the subject, wherein the hypoventilation determination unit may determine the hypoventilation condition by comparing the calculated biosignal parameter with the hypoventilation reference value, and the display control unit may control the display to display the calculated biosignal parameter.

According to an embodiment of the present inventive concept, the biosignal parameter may include numerical data on at least one of oxygen saturation, end tidal CO2, pulse wave, electrocardiogram, body temperature, and blood pressure.

According to an embodiment of the present inventive concept, the display control unit may control the display to display the image data including at least one of a real-time ventilation image, a normal ventilation range, a hypoventilation area, an apnea area, and the alarm information.

According to an embodiment of the present inventive concept, a hypoventilation monitoring method may include the steps of generating, by an EIT data processing unit, image data on the chest of a subject by measuring either current or voltage through a plurality of electrodes attached to the subject, calculating, by a ventilation parameter calculation unit, a ventilation parameter of the subject by analyzing an image change of the chest based on the generated image data, determining, by a hypoventilation determination unit, a hypoventilation condition by comparing the calculated ventilation parameter with a hypoventilation reference value, and controlling, by a display control unit, a display to display at least one of the generated image data, the calculated ventilation parameter, or the determined alarm information on the hypoventilation condition.

According to an embodiment of the present inventive concept, the hypoventilation monitoring method may further include calculating, by a biosignal parameter calculation unit, a biosignal parameter by measuring a biosignal through a sensor attached to the subject, wherein the determining of the hypoventilation condition may include determining the hypoventilation condition by comparing the calculated biosignal parameter with the hypoventilation reference value, and the controlling of the display may include controlling the display to display the calculated biosignal parameter.

Advantageous Effects

According to the present inventive concept, it is possible to continuously monitor hypoventilation by processing and interpreting simultaneously EIT images of a cross section of the chest including the lungs, and biosignals, such as oxygen saturation, end tidal CO2, pulse wave, electrocardiogram, blood pressure, and body temperature.

According to the present inventive concept, it is possible to improve the accuracy of measurement of tidal volume and minute ventilation by using an EIT image that provides information on air distribution and volume change in the lungs.

According to the present inventive concept, it is possible to display the homogeneity of an air distribution in the lungs together with the tidal volume, minute ventilation, and respiratory rate based on an EIT image.

According to the present inventive concept, it is possible to measure biosignals such as oxygen saturation, pulse wave, electrocardiogram, and blood pressure together in addition to an EIT system for imaging and quantifying hypoventilation.

According to the present inventive concept, it is possible to attach a plurality of electrodes at once or attach the plurality of electrodes separately by providing a sticky patch on one side of a plate.

According to the present inventive concept, it is possible to extract information about asymmetric ventilation of both lungs and heterogeneous ventilation in each lung from an EIT image and index and display the extracted information.

MODES FOR THE INVENTION

Figure 1:
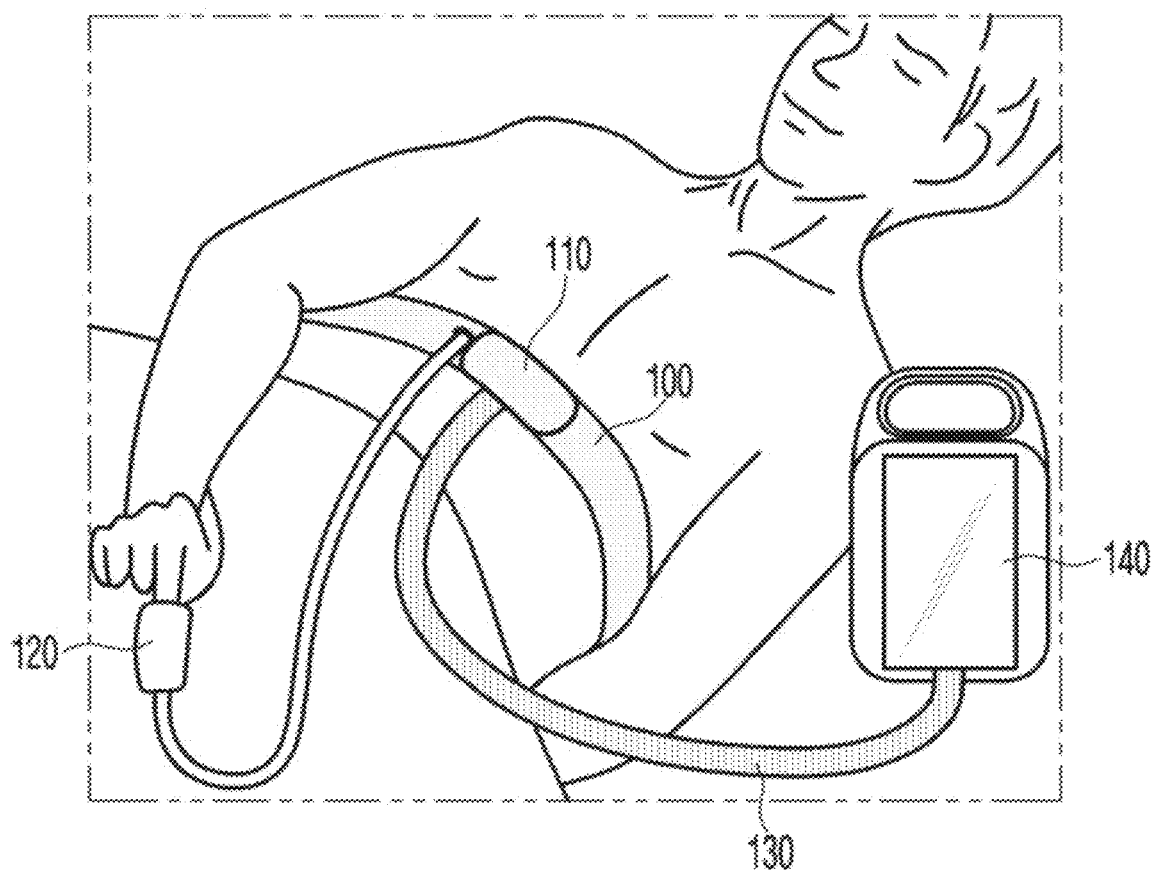
FIG. 1 is a diagram illustrating a wearing environment of a hypoventilation monitoring system according to an embodiment of the present inventive concept.

Hereinafter, various embodiments of the present disclosure will be described with reference to the accompanying drawings.

The embodiments and terms used therein are not intended to limit the technology described in the present disclosure to a specific embodiment, and it should be understood to include various modifications, equivalents, and/or substitutes of the embodiment.

Further, hereinafter, in describing various embodiments, detailed description of associated known functions or configurations will be omitted if it is determined that they unnecessarily make the gist of the present inventive concept unclear.

In addition, terms to be described below, as terms which are defined in consideration of functions in various embodiments, may vary depending on the intention of a user or an operator or usual practices. Accordingly, the terms need to be defined based on contents throughout this specification.

In connection with the description of the drawings, similar reference numerals may be used for similar components.

A singular form may include a plural form unless otherwise clearly meant in the contexts.

In the present disclosure, expressions such as "A or B" or "at least one of A and/or B" may include all available combinations of items listed together.

Expressions such as "first," and "second," can modify the corresponding components regardless of their order or importance, and will be used only to distinguish one component from another component, but are not limit the components.

When any (e.g., first) component is referred to as being "(functionally or communicatively) connected" or "accessed" to the other (e.g., second) component, the component may be directly connected to the other component, or may be connected through another component (e.g., a third component).

In this specification, "configured to" may be used interchangeably with, for example, "suitable for," "having the ability to," "changed to", "made to", "capable of", or "designed to" in hardware or software, depending on the situation.

In some situations, the expression "a device configured to" may mean that the device "capable of" together with other devices or parts.

For example, the phrase "a processor configured to perform A, B, and C" may mean a dedicated processor (e.g., an embedded processor) for performing the operation, or a general-purpose processor (e.g., a CPU or application processor) capable of performing the corresponding operations by executing one or more software programs stored in a memory device.

Also, the term 'or' means an inclusive logical sum 'inclusive or' rather than an exclusive logical sum 'exclusive or'.

That is, unless stated otherwise or unless clear from the context, the expression of 'x uses a or b' means any one of natural inclusive permutations.

Terms such as 'part' and 'unit' used herein mean a unit that processes at least one function or operation, which may be implemented by hardware or software or a combination of hardware and software.

FIG. 1 is a diagram illustrating a wearing environment of a hypoventilation monitoring system according to an embodiment of the present inventive concept.

Referring to FIG. 1, a hypoventilation monitoring system may continuously monitor hypoventilation using electrical impedance tomography (EIT).

According to an embodiment of the present inventive concept, the hypoventilation monitoring system may include an annular electrode belt 100 worn on a subject, a sensor unit including a sensor box 110 and a biometric sensor 120, and a hypoventilation monitoring unit 140.

As an example, the sensor box 110 may receive EIT data for the subject by coupling different ends of the electrode belt 100 to each other. For example, the EIT data may include impedance data for current and voltage measured through an electrode attached to the subject.

For example, the hypoventilation monitoring system may monitor image data on the chest of the subject using the electrode belt 100, and may monitor oxygen saturation, end tidal $CO_2$, pulse wave, electrocardiogram, blood pressure, body temperature, etc. using the biometric sensor 120.

In addition, the hypoventilation monitoring system may transmit health data of the subject collected using the electrode belt 100 and the biometric sensor 120 to the hypoventilation monitoring unit 140 using a cable. For example, the electrode belt 100 may also be referred to as an elastic belt.

In addition, the hypoventilation monitoring unit 140 may process the transmitted data and control the display to output a monitoring result for a hypoventilation condition of the subject.

Accordingly, according to the present inventive concept, it is possible to continuously monitor hypoventilation by processing and interpreting simultaneously EIT images of a cross section of the chest including the lungs, and biosignals, such as oxygen saturation, pulse wave, electrocardiogram, blood pressure, etc.

Figure 2:
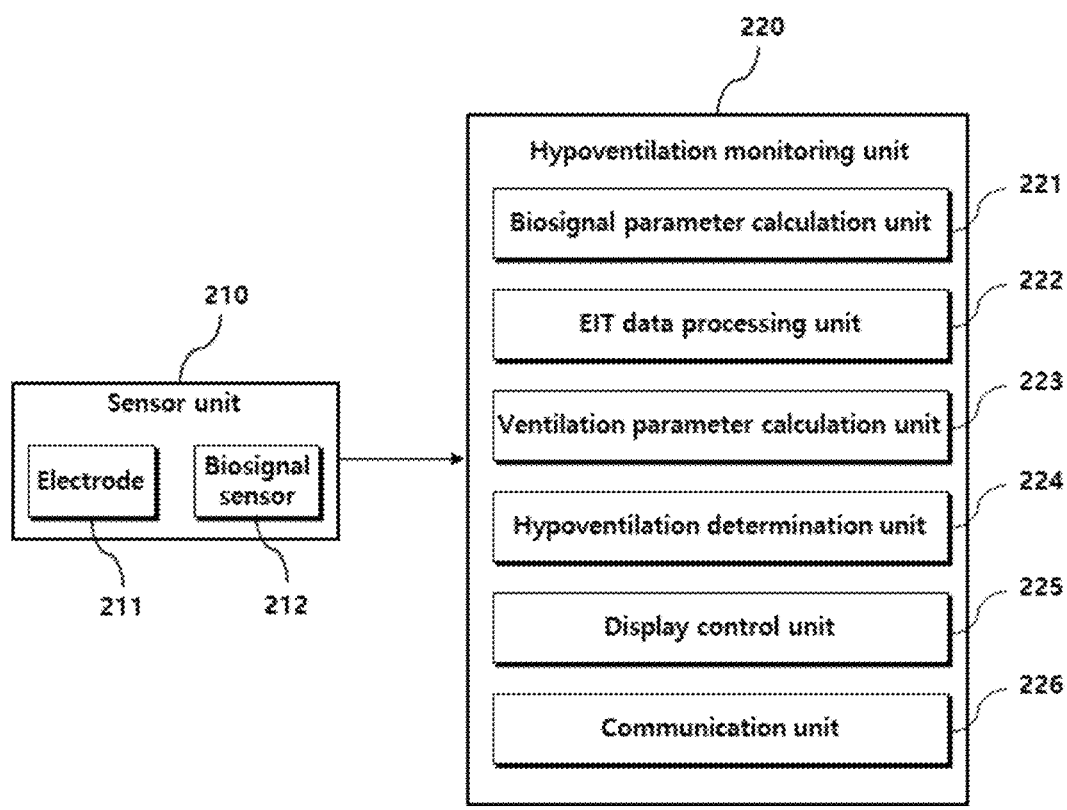
FIG. 2 is a diagram illustrating components of a hypoventilation monitoring system according to an embodiment of the present inventive concept.

FIG. 2 is a diagram illustrating components of a hypoventilation monitoring system according to an embodiment of the present inventive concept.

Referring to FIG. 2, according to an embodiment of the present inventive concept, the hypoventilation monitoring system may include a sensor unit 210 and a hypoventilation monitoring unit 220. For example, the hypoventilation monitoring unit 220 may also be referred to as a main body.

According to an embodiment of the present inventive concept, the hypoventilation monitoring unit 220 includes a biosignal parameter calculation unit 221, an EIT data processing unit 222, a ventilation parameter calculation unit 223, a hypoventilation determination unit 224 and a display control unit 225.

For example, the biosignal parameter calculation unit 221 may calculate a biosignal parameter by measuring a biosignal through a sensor attached to the subject.

According to an embodiment of the present inventive concept, the biosignal parameter calculation unit 221 may calculate a biosignal parameter including at least one of oxygen saturation, end tidal $CO_2$, pulse wave, electrocardiogram, body temperature and blood pressure.

For example, the biosignal parameter may include numerical data on at least one of oxygen saturation, end tidal $CO_2$, pulse wave, electrocardiogram, body temperature, and blood pressure.

According to an embodiment of the present inventive concept, the EIT data processing unit 222 may generate image data on the chest of the subject by measuring either current or voltage through a plurality of electrodes attached to the subject.

For example, the EIT data processing unit 222 may detect an air distribution condition in the lungs, including symmetry of the degree of ventilation of both lungs and homogeneity of the ventilation condition of each lung from the image data.

According to an embodiment of the present inventive concept, the EIT data processing unit 222 may quantify the air distribution and volume in the lungs by imaging the EIT data acquired through the electrodes attached to the chest.

That is, the EIT data processing unit 222 may generate image data associated with the air distribution and volume of the lungs located inside the chest based on the voltage or current measured through the electrodes attached to the chest.

According to an embodiment of the present inventive concept, the EIT data processing unit 222 may repeat such a measurement while injecting the current or voltage between the plurality of electrodes.

For example, the EIT data processing unit 222 may restore a change in electrical conductivity of a cross section of the chest into an image using measured voltage data induced by a plurality of injection currents.

According to an embodiment of the present inventive concept, the EIT data processing unit 222 may generate at least 10 EIT images based on either current or voltage measured through the electrodes.

According to an embodiment of the present inventive concept, the ventilation parameter calculation unit 223 may calculate a ventilation parameter of the subject by analyzing an image change of the chest based on the generated image data.

That is, the ventilation parameter calculation unit 223 may calculate, as a ventilation parameter, an image change of the chest from image data generated based on the EIT data measured through the plurality of electrodes located on the annular elastic belt.

Accordingly, according to the present inventive concept, it is possible to improve the accuracy of measurement of tidal volume and minute ventilation by using an EIT image that provides information on air distribution and volume change in the lungs.

For example, the ventilation parameter calculation unit 223 may calculate a ventilation parameter including tidal volume, minute ventilation, or respiratory rate by analyzing the image change.

According to an embodiment of the present inventive concept, the ventilation parameter calculation unit 223 may calculate a ventilation parameter based on the image change of the lung in the image.

As an example, the ventilation parameter calculation unit 223 determines a ventilation function degree of the subject based on the image change of the lung, and may calculate tidal volume, minute ventilation, and respiratory rate of the subject based on the inhalation and exhalation of the lungs as a result of the determination.

According to an embodiment of the present inventive concept, the hypoventilation determination unit 224 may determine a hypoventilation condition by comparing either the biosignal parameter or the ventilation parameter with a hypoventilation reference value.

As an example, the hypoventilation determination unit 224 may determine the hypoventilation condition when a value of either the biosignal parameter or the ventilation parameter is lower than the hypoventilation reference value.

For example, the hypoventilation determination unit 224 may determine a normal condition when the value of either the biosignal parameter or the ventilation parameter is higher than or equal to the hypoventilation reference value.

For example, the hypoventilation reference value may be calculated based on a change in area of the lung region of the chest based on the image data.

For example, the hypoventilation reference value may include numerical data corresponding to an area size of the lung region determined as hypoventilation.

According to an embodiment of the present inventive concept, the display control unit 225 may control the display to display at least one of image data, a biosignal parameter, a ventilation parameter, or alarm information on the hypoventilation condition.

For example, when displaying the inside of the chest based on the image data, the display control unit 225 may provide alarm information by controlling the display to reverse a color or display condition of a screen.

For example, the alarm information may be output using a sound or a color change of the screen.

For example, the display control unit 225 may control the display to display oxygen saturation, tidal volume, minute ventilation, or respiratory rate as numbers and signal graphs.

According to an embodiment of the present inventive concept, the display control unit 225 may control the display to display a biosignal parameter including at least one of oxygen saturation, end tidal CO2, pulse wave, electrocardiogram, body temperature, and blood pressure as numbers and signal graphs.

Accordingly, according to the present inventive concept, it is possible to measure biosignals such as oxygen saturation, end tidal CO2, pulse wave, electrocardiogram, body temperature or blood pressure together in addition to an EIT system for imaging and quantifying hypoventilation.

For example, the display control unit 225 may control the display to display image data including at least one of a real-time ventilation image, a normal ventilation range, a hypoventilation area, an apnea area, and alarm information.

According to another embodiment of the present inventive concept, the hypoventilation monitoring unit 220 may further include a communication unit 226.

According to an embodiment of the present inventive concept, the communication unit 226 may transmit the calculated ventilation parameter to at least one of a ventilator, an anesthetic machine, or a drug injector so as to change an operation of at least one of the ventilator, the anesthetic machine, or the drug injector.

The communication unit 226 may perform a conversion function between a baseband signal and a bit stream according to a physical layer standard of the system.

For example, when transmitting data, the communication unit 226 may generate complex symbols by encoding and modulating a transmission bit stream.

In addition, the communication unit 226 may restore a reception bit stream by demodulating and decoding a baseband signal when receiving data.

In addition, the communication unit 226 may up-convert the baseband signal to a radio frequency (RF) band signal and then transmit the up-converted RF band signal through an antenna, and down-convert the RF band signal received through the antenna into the baseband signal.

Further, the communication unit 226 may include a transmission filter, a reception filter, an amplifier, a mixer, an oscillator, a digital to analog converter (DAC), an analog to digital converter (ADC), and the like.

In addition, the communication unit 226 may include different communication modules to process signals at different frequency bands.

According to another embodiment of the present inventive concept, the hypoventilation monitoring system may further include a sensor unit 210.

For example, the sensor unit 210 may include electrodes 211 and a biosignal sensor 212.

According to an embodiment of the present inventive concept, the electrodes 211 are located at regular intervals inside the elastic belt, and may transmit the EIT data for current or voltage to the hypoventilation monitoring unit 220 through a cable of the sensor box connected to the elastic belt.

For example, the electrodes 211 are included in a plurality of stickers in a preset number, and may transmit the EIT data to the sensor box through an independent connection line for each of the plurality of stickers, or each of the electrodes 211 may be attached to the subject to transmit the EIT data to the sensor box through an independent connection line for each of the plurality of electrodes.

That is, each of the plurality of electrodes may be connected to the sensor box through an independent connection line for each of the plurality of electrodes to be connected to the sensor box in parallel.

Accordingly, according to the present inventive concept, it is possible to block a connection line for an electrode that collects error data among the plurality of electrodes and measure either current or voltage through the remaining electrodes that are not blocked.

According to an embodiment of the present inventive concept, a plurality of electrodes 211 may be configured.

According to an embodiment of the present inventive concept, the biosignal sensor 212 may measure at least one of oxygen saturation, pulse wave, electrocardiogram, or blood pressure of the subject.

For example, the biosignal sensor 212 may be worn on a subject's finger or included in an electrode belt.

In addition, the hypoventilation monitoring system according to an embodiment of the present inventive concept further includes an alarm unit (not illustrated), and the alarm unit (not illustrated) may preset a normal range of each of measurement information and generate an alarm by means of a screen, a sound, or communication when the measurement information is out of the normal range.

In addition, the hypoventilation monitoring system may store and transmit all measured images, signals, numerical information, alarm occurrence time and alarm contents as digital data.

According to an embodiment of the present inventive concept, the sensor box may provide EIT data to the hypoventilation monitoring unit 220 connected by a cable.

According to an embodiment of the present inventive concept, the sensor box may provide EIT data in real time, provide the EIT data based on a predetermined period, or provide the EIT data when a value of the EIT data is measured as a specific reference value or more. Here, the specific reference value may correspond to a hypoventilation reference value.

Figure 3A:
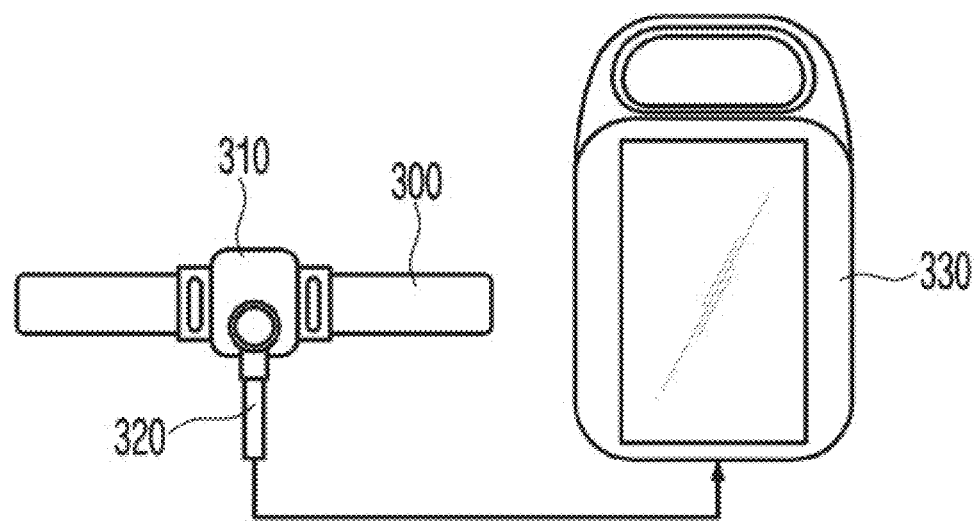
FIGS. 3A to 3C are diagrams illustrating a hypoventilation monitoring system using an integrated electrode belt according to an embodiment of the present inventive concept.
Figure 3B:
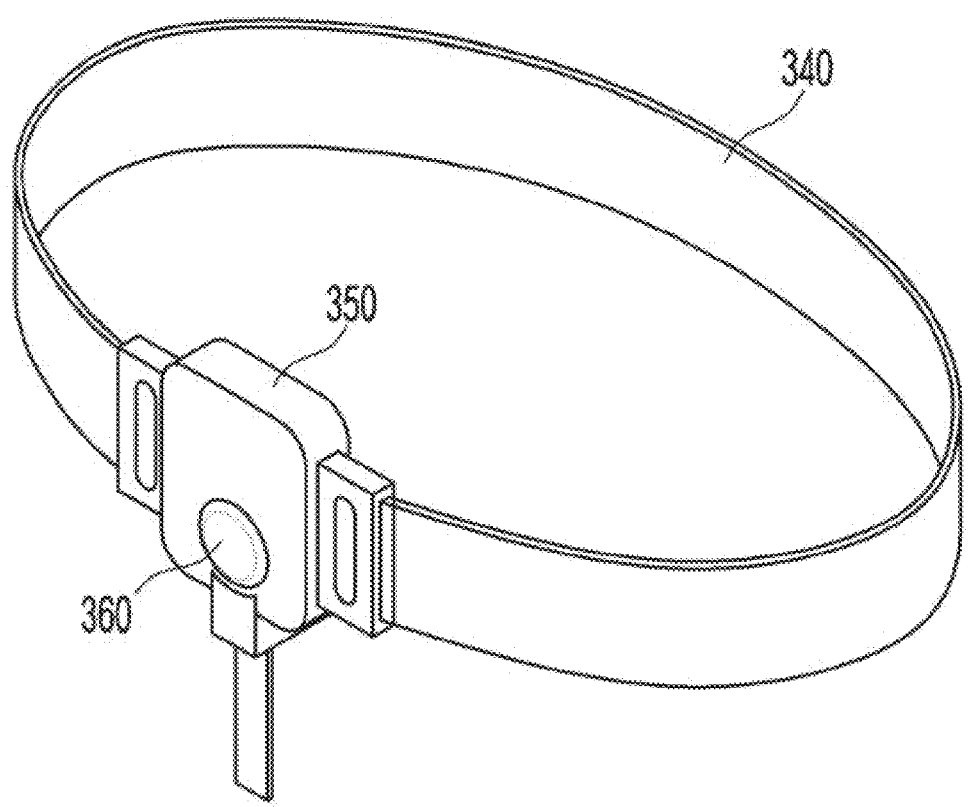
Figure 3C:
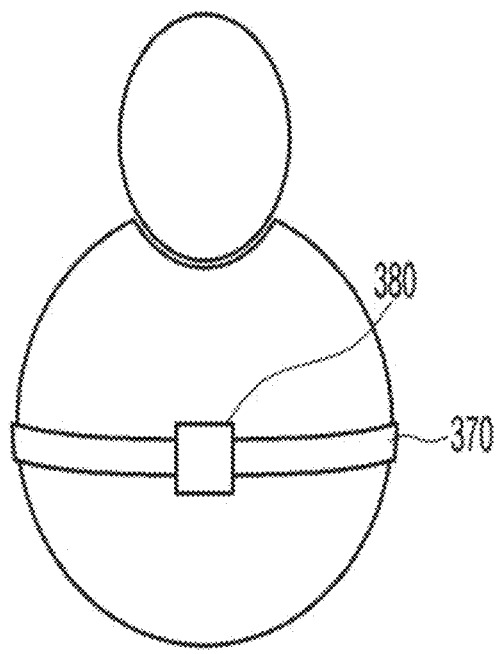

FIGS. 3A to 3C are diagrams illustrating a hypoventilation monitoring system using an integrated electrode belt according to an embodiment of the present inventive concept.

Referring to FIG. 3A, both ends of an electrode belt 300 are coupled to a sensor box 310, and the electrode belt 300 may have an annular shape.

In addition, the sensor box 310 may be connected to a hypoventilation monitoring unit 330 through a cable 320. For example, the hypoventilation monitoring unit 330 may also be referred to as a hypoventilation monitoring device.

For example, a plurality of electrodes may be located inside the electrode belt 300.

The hypoventilation monitoring unit 330 may display a health condition of a subject by controlling a display.

Referring to FIG. 3B, both ends of the electrode belt 340 according to an embodiment of the present inventive concept may be coupled to the sensor box 350. The electrode belt 340 may have an annular shape by covering the circumference of the subject's chest.

As an example, both ends of the electrode belt 340 may be simultaneously separated from the sensor box 350 or any one of the both ends thereof may be separated from the sensor box 350 by the pressure on the button 360.

Referring to FIG. 3C, an electrode belt 370 according to an embodiment of the present inventive concept is worn along a circumference of a specific part of the subject, and may collect EIT data associated with the subject from electrodes located therein, and transmit the collected EIT data to a sensor box 380.

FIGS. 4A to 4E are diagrams illustrating a hypoventilation monitoring system using sticker-type electrodes according to an embodiment of the present inventive concept.

Figure 4A:
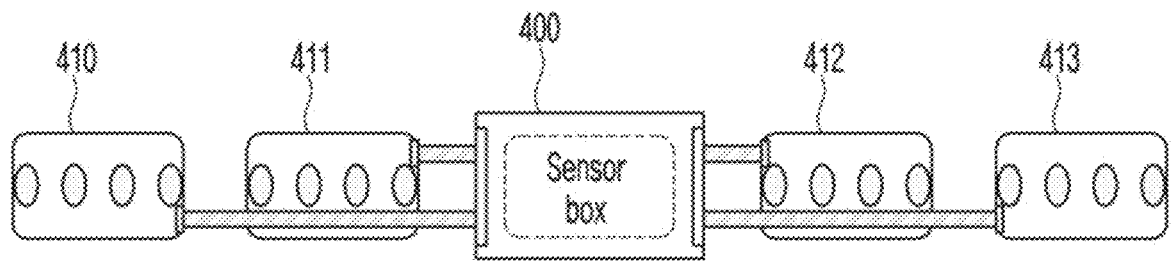
FIGS. 4A to 4E are diagrams illustrating a hypoventilation monitoring system using sticker-type electrodes according to an embodiment of the present inventive concept.

Referring to FIG. 4A, the hypoventilation monitoring system according to an embodiment of the present inventive concept may measure EIT data using a plurality of stickers 410, 411, 412, and 413.

According to an embodiment of the present inventive concept, electrodes are included in a plurality of stickers in a preset number to transmit the EIT data to a sensor box 400 through an independent connection line for each of the plurality of stickers.

When describing one of the plurality of stickers 410, 411, 412, 413, the sticker 410 includes four electrodes. Four electrodes form electrode pairs, wherein two electrodes apply current or voltage, and the other two electrodes may measure current or voltage.

The sensor box 400 of the present inventive concept may receive EIT data of a subject through an independent connection line for each of the plurality of stickers 410, 411, 412, and 413.

Figure 4B:
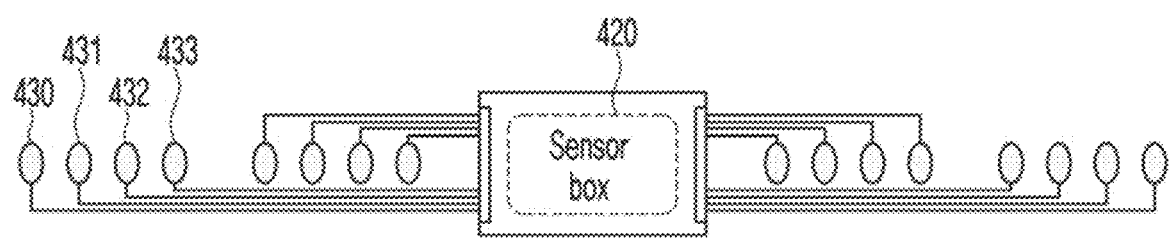

Referring to FIG. 4B, the hypoventilation monitoring system according to an embodiment of the present inventive concept may measure EIT data using a plurality of electrode patches 430, 431, 432, and 433. Here, reference numerals for the plurality of electrode patches have been only partially written, but the plurality of electrode patches connected to the sensor box 420 may be operated as described below.

For example, each of the plurality of electrode patches 430, 431, 432, and 433 may be attached to the subject to transmit the EIT data to the sensor box 420 through an independent connection line for each of the plurality of electrodes.

In the present inventive concept, even when a subject is obese or has a lot of hair on the chest, a plurality of electrodes may be separately attached to efficiently measure EIT data of the subject.

Further, according to the present inventive concept, it is possible to attach a plurality of electrodes at once or attach the plurality of electrodes separately by providing a sticky patch on one side of a plate.

Figure 4C:
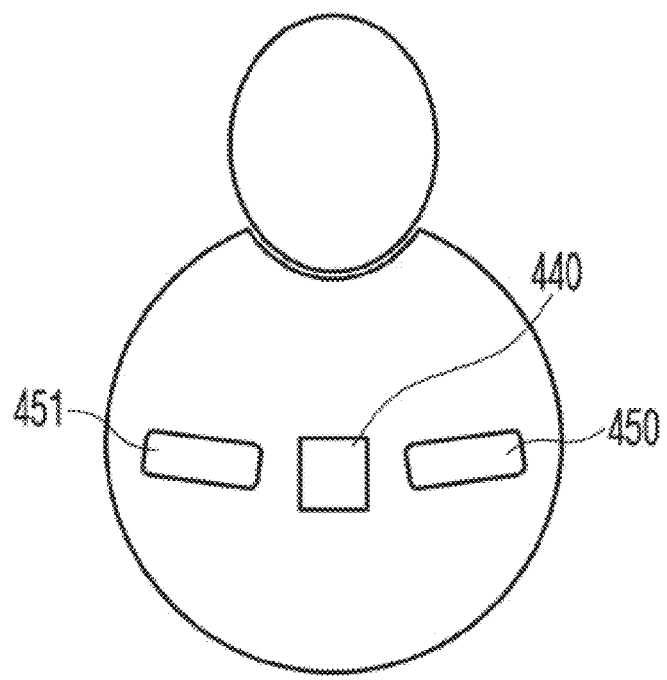

Referring to FIG. 4C, an electrode belt 440 according to an embodiment of the present inventive concept is attached and worn on a specific part of the subject, and may collect EIT data associated with the subject from electrodes located therein, and transmit the collected EIT data to a sensor box 440.

Figure 4D:
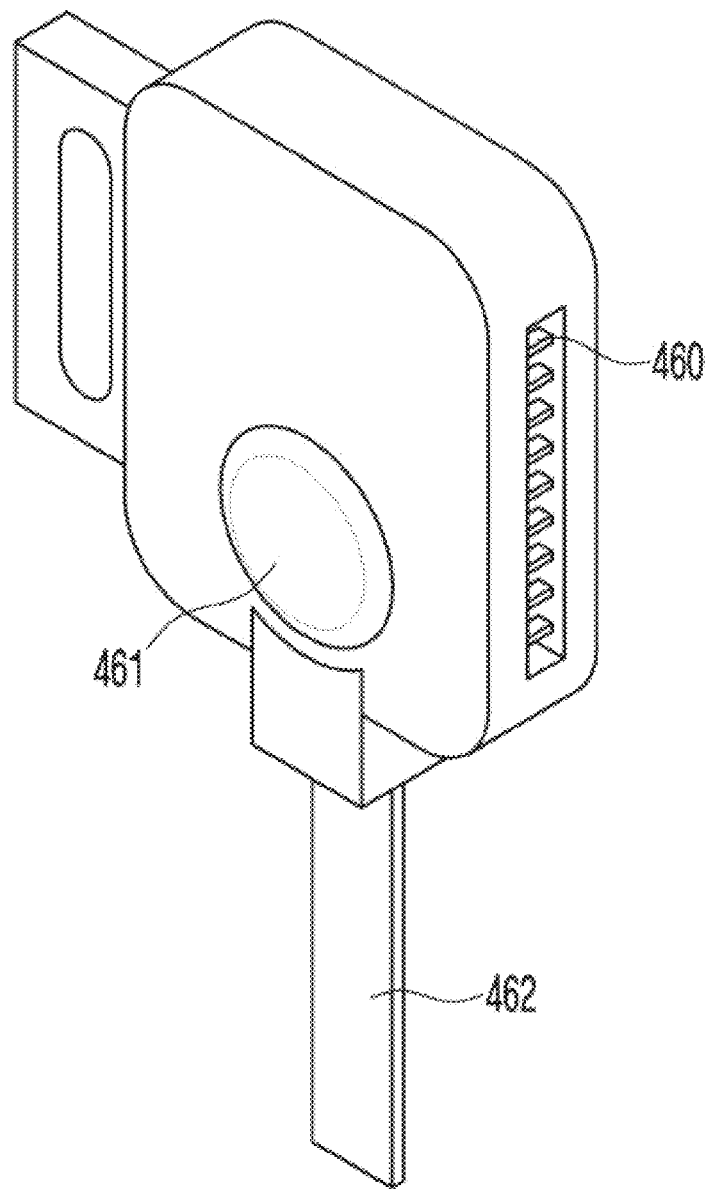

Referring to FIG. 4D, the sensor box according to an embodiment of the present inventive concept may include a plurality of holes 460 into which each of a plurality of connection lines may be inserted.

In addition, when pressure to a button 461 is input on the sensor box, each of the connection lines inserted through the plurality of holes 460 may be separated from the sensor box.

In addition, a cable 462 connected to the sensor box may transmit EIT data collected through a plurality of electrode patches to a hypoventilation monitoring unit.

Figure 4E:
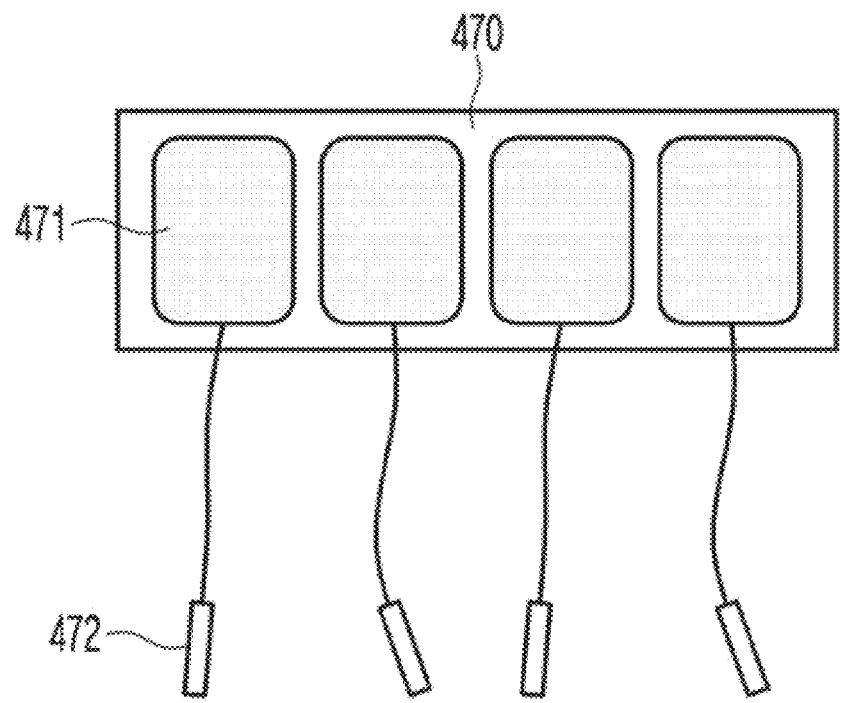

Referring to FIG. 4E, an electrode 471 included in a sticker 470 may collect EIT data and transmit the collected EIT data to the hypoventilation monitoring unit through a connection line 472. For example, the EIT data may include impedance data based on the measured current or voltage.

Figure 5:
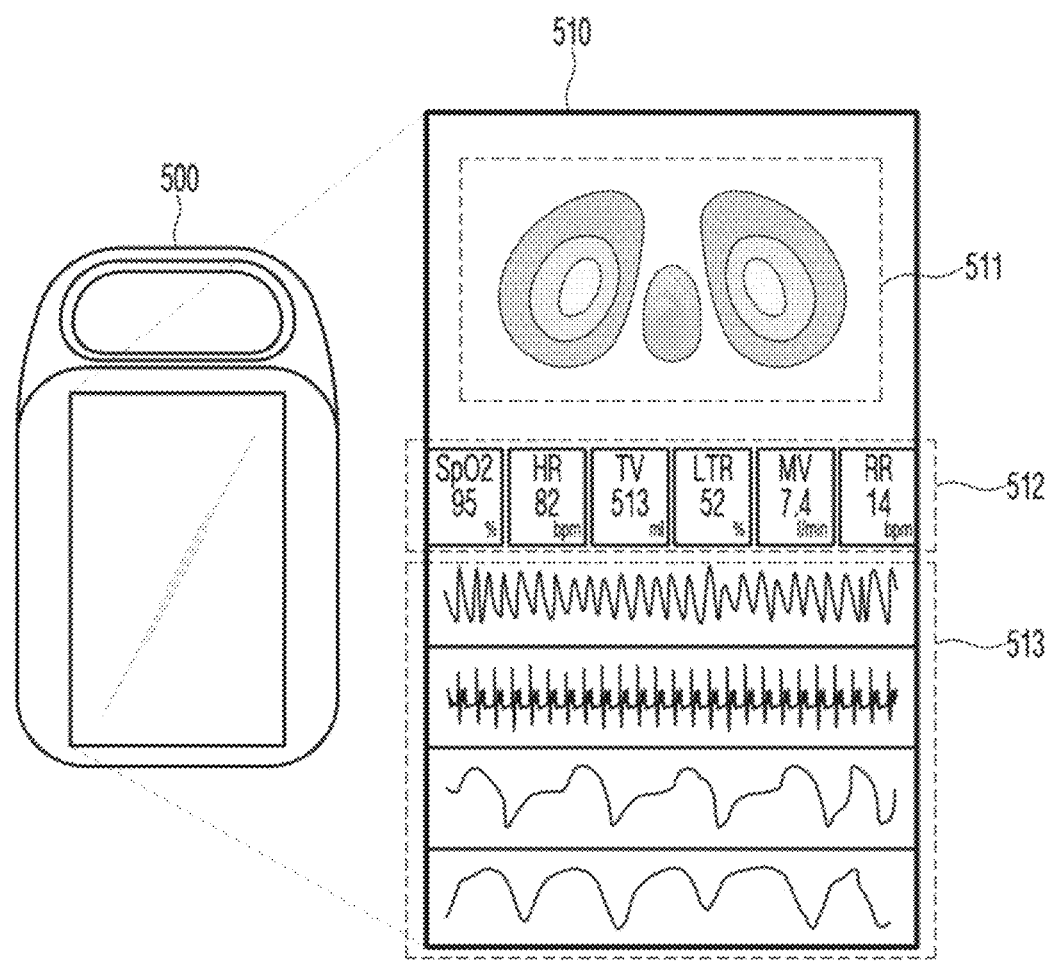
FIG. 5 is a diagram illustrating a display of a hypoventilation monitoring system according to an embodiment of the present inventive concept.

FIG. 5 is a diagram illustrating a display of a hypoventilation monitoring system according to an embodiment of the present inventive concept.

Referring to FIG. 5, a hypoventilation monitoring unit 500 may control a display 510 to output an image 511, a numerical value 512, and a graph 513 on a display 510.

According to an embodiment of the present inventive concept, the hypoventilation monitoring unit 500 may display inhalation and exhalation of a lung region of a subject through the image 511.

As an example, the hypoventilation monitoring unit 500 may control the display to output any one of a real-time ventilation image, a normal ventilation range, a hypoventilation area, an apnea area, or an alarm through the image 511.

Accordingly, according to the present inventive concept, it is possible to display the homogeneity of an air distribution in the lungs together with tidal volume, minute ventilation, and respiratory rate based on an EIT image.

According to an embodiment of the present inventive concept, the hypoventilation monitoring unit 500 may control the display to output oxygen saturation (SpO2), end tidal CO2 (ETCO2), heart rate (HR), tidal volume (TV), inspiratory time ratio (ITR), minute ventilation (MV), and respiration rate (RR) through the numerical value 512.

That is, the hypoventilation monitoring unit 500 may control the display to output various indicators representing the health condition of the subject using numbers.

Further, the hypoventilation monitoring unit 500 may extract information about asymmetric ventilation of both lungs and heterogeneous ventilation in each lung from an EIT image and index and display the extracted information.

According to an embodiment of the present inventive concept, the hypoventilation monitoring unit 500 may control the display to output photoplethysmography (PPG), electrocardiography (ECG), nasal pressure, and tidal volume (TV) through the graph 513.

Accordingly, according to the present inventive concept, it is possible to extract information about asymmetric ventilation of both lungs and heterogeneous ventilation in each lung from the EIT image and index and display the extracted information.

Figure 6:
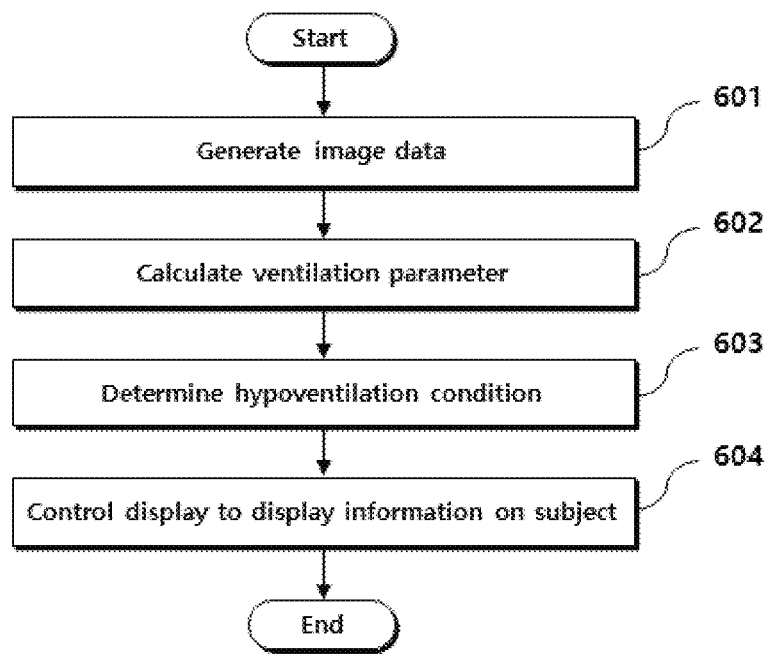
FIG. 6 is a diagram illustrating a flowchart associated with a hypoventilation monitoring method according to an embodiment of the present inventive concept.

FIG. 6 is a diagram illustrating a flowchart associated with a hypoventilation monitoring method according to an embodiment of the present inventive concept.

Referring to FIG. 6, in step 601, the hypoventilation monitoring method may generate image data.

That is, the hypoventilation monitoring method may generate image data on the chest of a subject by measuring either current or voltage through a plurality of electrodes attached to the subject.

In step 602, the hypoventilation monitoring method may calculate a ventilation parameter.

That is, the hypoventilation monitoring method may calculate a ventilation parameter of the subject by analyzing an image change of the chest based on the generated image data.

In step 603, the hypoventilation monitoring method may determine a hypoventilation condition.

That is, the hypoventilation monitoring method may determine a hypoventilation condition by comparing the ventilation parameter with a hypoventilation reference value. Here, the hypoventilation reference value may include numerical information for determining hypoventilation.

According to another embodiment, the hypoventilation monitoring method may determine a hypoventilation condition by comparing a biosignal parameter with a hypoventilation reference value.

In step 604, the hypoventilation monitoring method may control a display to display information on the subject.

That is, the hypoventilation monitoring method may control the display to display at least one of image data, a ventilation parameter, or alarm information on a hypoventilation condition.

According to another embodiment, the hypoventilation monitoring method may control the display to display a biosignal parameter.

The method according to the embodiment may be implemented in a form of program instructions which may be performed through various computer means to be recorded in a computer readable medium. The computer readable medium may include program instructions, a data file, a data structure, and the like alone or in combination.

The program instructions recorded in the medium may be specially designed and configured for the embodiments or may be known and used by those skilled in a computer software field. An example of the computer readable medium includes magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program instructions.

Examples of the program instructions include high-level language codes executable by a computer by using an interpreter, and the like, as well as machine language codes created by a compiler. The hardware devices may be configured to operate as one or more software modules in order to perform the operations of the embodiments, and vice versa.

As described above, although the embodiments have been described by the limited embodiments and the drawings, various modifications and variations are possible from the above description by those skilled in the art. For example, even if the described techniques are performed in a different order from the described method, and/or components such as a system, a structure, a device, a circuit, etc. described are coupled or combined in a different form from the described method, or replaced or substituted by other components or equivalents, an appropriate result can be achieved.

Therefore, other implementations, other embodiments, and equivalents to the appended claims fall within the scope of the claims to be described below.

The invention claimed is:

1. A hypoventilation monitoring system comprising:
a sensor box configured to measure an EIT data on a chest of a subject and transmit the measured EIT data in real-time; and
a hypoventilation monitoring unit configured to receive the EIT data from the sensor box, monitor a hypoventilation condition of the subject by using the received EIT data, and display the monitoring result for the hypoventilation condition,
wherein the hypoventilation monitoring unit comprises:
an EIT data processing unit configured to detect a ventilation condition information comprising an air distribution, volume change, or combinations thereof inside lungs from the EIT data;
a ventilation parameter calculation unit configured to calculate a ventilation parameter comprising tidal volume, minute ventilation, or respiratory rate by analyzing the detected ventilation condition information;
a hypoventilation determination unit configured to determine a hypoventilation condition by comparing the calculated ventilation parameter with a hypoventilation reference value; and
a display control unit configured to control a display to display at least one of the calculated ventilation parameter or the monitoring result for the hypoventilation condition.

2. The hypoventilation monitoring system of claim 1, wherein the EIT data processing unit is further configured to detect the ventilation condition information inside the lungs from a change in electrical conductivity of a cross section of the chest from the EIT data measured at least one of current or voltage through a plurality of electrodes attached to the subject.

3. The hypoventilation monitoring system of claim 2, wherein the hypoventilation determination unit is further configured to determine the hypoventilation condition by comparing the calculated each of the ventilation parameters with the hypoventilation reference value calculated based on the change in electrical conductivity of the cross section of the chest or with the hypoventilation reference value displayed with a numerical data corresponding to an area size for electrical conductivity in a lung region.

4. The hypoventilation monitoring system of claim 3, wherein the display control unit is configured to control the display to display tidal volume, minute ventilation, or respiratory rate as numbers and signal graphs.

5. The hypoventilation monitoring system of claim 1, wherein the display control unit is further configured to control the display to display a biosignal parameter including at least one of oxygen saturation, end tidal CO2, pulse wave, electrocardiogram, body temperature, or blood pressure as numbers and signal graphs.

6. The hypoventilation monitoring system of claim 1, further comprising:
a communication unit configured to transmit the calculated ventilation parameter to at least one of a ventilator, an anesthetic machine, or a drug injector to change an operation of at least one of the ventilator, the anesthetic machine, or the drug injector.

7. The hypoventilation monitoring system of claim 1, further comprising:
a biosignal parameter calculation unit configured to calculate a biosignal parameter by measuring a biosignal through a sensor attached to the subject,
wherein the hypoventilation determination unit is further configured to determine the hypoventilation condition by comparing the calculated biosignal parameter with the hypoventilation reference value, and
the display control unit is further configured to control the display to display the calculated biosignal parameter.

8. The hypoventilation monitoring system of claim 1, wherein the hypoventilation monitoring unit further comprises:
an alarm unit configured to preset a normal range for determine the hypoventilation condition for each of the calculated ventilation parameter, and generate alarm information by means of a screen, a sound, or a communication when the calculated parameter is out of the normal range,
wherein the display control unit is further configured to control the display to display at least one of the alarm information for the determined hypoventilation condition.

9. A hypoventilation monitoring method comprising:
measuring, in a sensor box, an EIT data on a chest of a subject in real-time and transmitting the measured EIT data; and
receiving, in a hypoventilation monitoring unit, the EIT data from the sensor box, monitoring hypoventilation condition of the subject by using the received EIT data, and displaying the monitoring result for the hypoventilation condition,
wherein the displaying of the monitoring result comprising:
detecting, by an EIT data processing unit, a ventilation condition information comprising an air distribution, volume change, or combinations thereof inside lungs from the EIT data;
calculating, by a ventilation parameter calculation unit, a ventilation parameter comprising tidal volume, minute ventilation, or respiratory rate by analyzing the detected ventilation condition information;
determining, by a hypoventilation determination unit, a hypoventilation condition by comparing the calculated ventilation parameter with a hypoventilation reference value; and
controlling, by a display control unit, a display to display at least one of the calculated ventilation parameter, or the monitoring result for the hypoventilation condition.

10. The hypoventilation monitoring method of claim 9, wherein the detecting of the ventilation condition information comprises:
detecting the ventilation condition information inside the lungs from a change in electrical conductivity of a cross section of the chest from the EIT data measured at least one of current or voltage through a plurality of electrodes attached to the subject.

11. The hypoventilation monitoring method of claim 10, wherein the determining of a hypoventilation condition comprises:
determining the hypoventilation condition by comparing the calculated each of the ventilation parameters with the hypoventilation reference value calculated based on the change in electrical conductivity of the cross section of the chest or with the hypoventilation reference value displayed with a numerical data corresponding to an area size for electrical conductivity in a lung region.

12. The hypoventilation monitoring method of claim 9, wherein the controlling of the display comprises:
controlling the display to display tidal volume, minute ventilation, or respiratory rate as numbers and signal graphs.

* * * * *